United States Patent
Hildebrandt et al.

(10) Patent No.: US 6,482,917 B1
(45) Date of Patent: Nov. 19, 2002

(54) METHOD FOR PRODUCING POWDER-SHAPED CROSS-LINKED POLYMERIZATES

(75) Inventors: Volker Hildebrandt, Mannheim; Reinhold Dieing, Schifferstadt; Katrin Zeitz, Ludwigshafen, all of (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 09/720,916

(22) PCT Filed: Jul. 12, 1999

(86) PCT No.: PCT/EP99/04868

§ 371 (c)(1), (2), (4) Date: Jan. 2, 2001

(87) PCT Pub. No.: WO00/05274

PCT Pub. Date: Feb. 3, 2000

(30) Foreign Application Priority Data

Jul. 24, 1998 (DE) .......................... 198 33 287

(51) Int. Cl.$^7$ .................................. C08G 69/14
(52) U.S. Cl. .............. 528/323; 528/310; 528/315; 528/317; 528/422; 528/495; 528/502 C; 528/503
(58) Field of Search .................. 528/323, 310, 528/315, 317, 422, 495, 502 C, 503

(56) References Cited

U.S. PATENT DOCUMENTS

| | | |
|---|---|---|
| 4,748,220 A | 5/1988 | Hartmann |
| 5,804,662 A | 9/1998 | Schade |
| 6,015,551 A | 1/2000 | Schade |

FOREIGN PATENT DOCUMENTS

| | | |
|---|---|---|
| CA | 1262995 | * 11/1989 |
| DE | 195 46698 | 6/1997 |
| EP | 220 603 | 5/1987 |
| EP | 239 035 | 9/1987 |

* cited by examiner

*Primary Examiner*—Duc Truong
(74) *Attorney, Agent, or Firm*—Keil & Weinkauf

(57) ABSTRACT

A process for the preparation of pulverulent, cationic, crosslinked polymers based on monoethylenically unsaturated monomers containing a quaternized or quaternizable nitrogen atom comprises carrying out the polymerization in supercritical carbon dioxide as inert diluent with mixing at from 31° C. to 150° C. and above 73 bar.

3 Claims, No Drawings

METHOD FOR PRODUCING POWDER-SHAPED CROSS-LINKED POLYMERIZATES

The present invention relates to a process for the preparation of pulverulent, cationic, crosslinked polymers based on monoethylenically unsaturated monomers containing a quaternized or quaternizable nitrogen atom, by free-radical polymerization in supercritical carbon dioxide.

It is known in general terms that supercritical carbon dioxide can be used as solvent in the preparation of polymers by free-radical polymerization. For example, EP-A 220 603 describes a process for the preparation of uncrosslinked, pulverulent polymers based on N-vinyl monomers and/or ethylenically unsaturated carboxylic esters by free-radical polymerization in supercritical carbon dioxide. EP-A 239 035 describes the preparation of crosslinked, pulverulent polymers based on monoethylenically unsaturated carboxylic acids, or amides and/or esters thereof by polymerization in supercritical carbon dioxide. In the known processes, the reaction mixture and liquid carbon dioxide are generally introduced into a pressure vessel, and the supercritical state induced by increasing the temperature and pressure. However, it is disadvantageous here that the different solubilities of the monomers and crosslinking agents in the solvent means that products of nonuniform morphology or nonuniform chemical composition may be formed.

It is an object of the present invention to find an improved process for the preparation of crosslinked polymers.

We have found that this object is achieved by a process for the preparation of pulverulent, cationic, crosslinked polymers based on monoethylenically unsaturated monomers containing a quaternized or quaternizable nitrogen atom by free-radical-initiated polymerization, which comprises carrying out the polymerization in supercritical carbon dioxide as inert diluent with mixing at from 31° C. to 150° C. and above 73 bar.

The polymerization is carried out under pressure in supercritical carbon dioxide as inert diluent. The properties of carbon dioxide in the liquid and supercritical states have been reported by J. A. Hyatt, J. Org. Chem. 49, (1984), 5097-5101. According to this article, the critical point of carbon dioxide is at about 31° C. and 73 bar. The polymerization is preferably carried out under pressure in supercritical carbon dioxide at above about 31° C., the critical temperature of carbon dioxide. The upper temperature limit for the preparation of the polymers is 10° C. above the commencement of this softening range of the respective polymers formed. For most polymers, the upper value for this temperature limit is 150° C. The polymerization is preferably carried out at from 30 to 130° C. The reaction temperature need not be kept constant; it is also possible to set up a stepped or ramped temperature profile. It is advisable to set the temperatures at the beginning of the reaction to values in the range from 31 to 100° C. The pressures are above 73 bar, preferably in the range from 80 to 300 bar, particularly preferably from 120 to 250 bar.

The novel process is preferably carried out by firstly introducing carbon dioxide in the solid, liquid or gaseous state into the reaction space of a pressure apparatus which is conventional per se, then converting the carbon dioxide into the supercritical state by increasing the pressure to above 73 bar and the temperature to above 31° C., then setting the reaction temperature, and subsequently metering in the starting materials. The starting materials, such as monomers, free-radical initiators, crosslinking agents and, if desired, polymerization regulators, may be metered in individually or in the form of mixtures. Thus, it may be advisable, for example, to dissolve the free-radical initiators in the monomers. The procedure selected depends essentially on the solubilities of the individual components in one another and in the diluent. However, it is also possible to introduce all or some of the starting materials into the reaction space and then to add the carbon dioxide. If desired, starting materials can be metered in during the reaction (semibatch procedure).

The polymerization reaction is initiated with the aid of polymerization initiators which decompose to form free radicals. It is possible to use all initiators which are known for the polymerization of the monomers, for example initiators which decompose to form free radicals with half-value periods of less than 3 hours at the selected temperature. If the polymerization is carried out at different temperatures by starting the polymerization of the monomers at a low temperature and completing the polymerization at a significantly higher temperature, it is advantageous to use at least two different initiators which have an adequate decomposition rate in the temperature range selected in each case.

Based on 100 parts by weight of the monomer mixture, from 100 to 3000 parts by weight, preferably from 200 to 1500 parts by weight, of carbon dioxide are used. The carbon dioxide is preferably anhydrous. The polymerization reaction can be carried out batchwise or continuously with mixing of the reactants in pressure apparatuses of appropriate design. In order to dissipate the heat formed during the polymerization, it is desirable for the pressure apparatuses to have a cooling system. They must of course also be heatable in order to heat the reaction mixture to the respective temperature desired for the polymerization. The pressure apparatuses should have mixing means, for example stirrers (blade, impeller, multistage pulsed countercurrent or ribbon stirrers) or vanes.

The novel process is particularly suitable for the preparation of pulverulent, cationic, crosslinked polymers.

These pulverulent, cationic, crosslinked polymers are obtainable by free-radical-initiated polymerization of (a1) from 1 to 99.99% by weight of a free-radical-polymerizable monomer containing a quaternized or quaternizable nitrogen atom, or a mixture of such monomers, (a2) from 5 to 95% by weight of an N-vinyllactam, (b) from 0.01 to 20% by weight of a monomer which effects crosslinking, and (c) from 0 to 50% by weight of a further free-radical-copolymerizable monomer.

Suitable monomers (a1) are selected from one of the following groups:

N-vinylimidazole derivatives of the formula (I)

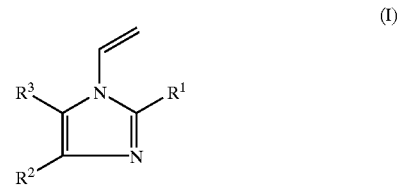

in which $R^1$, $R^2$ and $R^3$, independently of one another, are hydrogen, $C_1$–$C_4$-alkyl or phenyl, preferably 2-methyl-N-vinylimidazole or N-vinylimidazole;

N,N-diallylamines of the formula (II),

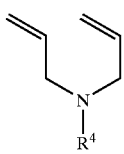

(II)

in which $R^4$ is a $C_1$–$C_{24}$-alkyl radical, preferably N,N-diallyl -N-methylamine.

Under the polymerization conditions in accordance with the invention, such diallylamines react with ring closure:

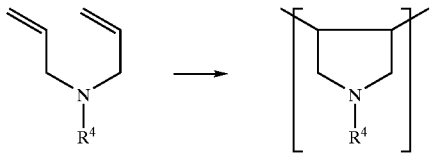

N,N-dialkylaminoalkyl derivatives of acrylic or methacrylic acid, of the formula (III)

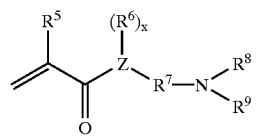

(III)

in which $R^5$ and $R^6$, independently of one another, are hydrogen or methyl, Z is a nitrogen atom where X=0, $R^7$ is a linear or branched $C_1$–$C_{24}$-alkylene radical, and $R^8$ and $R^9$, independently of one another, are $C_1$–$C_{24}$-alkyl radicals.

Suitable monomers of the formula (III) are, for example, N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N,N-dimethylaminobutyl (meth)acrylate, N,N-diethylaminobutyl (meth)acrylate, N,N-dimethylaminohexyl (meth)acrylate, N,N-dimethylaminooctyl (meth)acrylate, N,N-dimethylaminododecyl (meth)acrylate, N-[3-(dimethylamino)propyl]acrylamide, N-[3-(dimethylamino)butyl]methacrylamide, N-[8-(dimethylamino)octyl]methacrylamide, N-[12-(dimethylamino)dodecyl]-methacrylamide, N-[3-(diethylamino)propyl]methacrylamide and N-[3-(diethylamino)propyl]acrylamide, and mixtures thereof.

Preferred monomers (a1) are 3-methyl-1-vinylimidazolium chloride and methosulfate, dimethyldiallylammonium chloride, and N,N-dimethylaminoethylmethacrylate and N-[3-(dimethylamino)propyl]methacrylamide, each of which has, if desired, been quaternized by methyl chloride, dimethyl sulfate or diethyl sulfate.

Particularly preferred monomers (a1) are 3-methyl-1-vinylimidazolium chloride and methosulfate and dimethyl-diallylammonium chloride; very particularly preferred monomers (a1) are 3-methyl-1-vinylimidazolium chloride and methosulfate.

It is also possible to use mixtures of the monomers (a1).

Preferably, from 5 to 70% by weight, particularly preferably from 10 to 50% by weight, of the monomers (a1) are employed.

The monomers (a1) can either be used as monomers in quaternized form or polymerized in unquaternized form; in the latter case, the resultant copolymer is either quaternized or protonated. If the monomers are used in quaternized form, they can be employed either as dried substances or in the form of concentrated solutions in solvents which are suitable for the monomers, for example in polar solvents, such as water, methanol, ethanol, acetone or electrolyte solutions.

The protonation can be carried out, for example, using mineral acids, such as HCl, $H_2SO_4$, or monocarboxylic acids, for example formic acid or acetic acid, dicarboxylic acids or polybasic carboxylic acids, for example oxalic acid or citric acid, or any other proton-releasing compounds or substances which are capable of protonating the corresponding nitrogen atom. Water-soluble acids are particularly suitable for protonation.

The protonation of the polymer can be carried out either after the polymerization or during formulation of the cosmetic preparation, during which a physiologically compatible pH is generally established.

The term protonation is taken to mean at least some of the protonatable groups of the polymer, preferably from 20 to 100%, are protonated, resulting in a cationic overall charge of the polymer.

The quaternization of the compounds of the formulae (I) to (III) is carried out, for example, using alkyl halides having 1 to 24 carbon atoms in the alkyl group, for example methyl chloride, methyl bromide, methyl iodide, ethyl chloride, ethyl bromide, propyl chloride, hexyl chloride, dodecyl chloride, lauryl chloride or benzyl halide, in particular benzyl chloride or benzyl bromide. Other suitable quaternizing agents are dialkyl sulfates, in particular dimethyl sulfate or diethyl sulfate. The quaternization of the basic monomers of the formulae (I) to (III) can also be carried out using alkylene oxides, such as ethylene oxide or propylene oxide, in the presence of acids.

The quaternization of the monomers or of a polymer using one of said quaternizing agents can be carried out by methods which are known in general terms.

Preferred quaternizing agents are methyl chloride, dimethyl sulfate and diethyl sulfate.

Suitable monomers (a2) are N-vinyllactams, for example N-vinylpiperidone, N-vinylpyrrolidone and N-vinylcaprolactam, preferably N-vinylpyrrolidone.

Suitable crosslinking agents (monomers (b)) are, for example, acrylates, methacrylates, allyl ethers and vinyl ethers of at least dihydric alcohols. Some or all of the OH groups of the parent alcohols may have been etherified or esterified; however, the crosslinking agents contain at least two ethylenically unsaturated groups.

Examples of parent alcohols are dihydric alcohols, such as 1,2-ethanediol, 1,2-propanediol, 1,3-butanediol, 2,3-butanediol, 1,4-butanediol, but-2-ene-1,4-diol, 1,2-pentanediol, 1,5-pentanediol, 1,2-hexanediol, 1,5-hexanediol, 1,10-decanediol, 1,2-dodecanediol, 1,12-dodecanediol, neopentyl glycol, 3-methylpentane-1,5-diol, 2,5-dodecanediol, 1,12-dodecanediol, neopentyl glycol, 3-methylpentane-1,5-diol, 2,5-dimethyl-1,3-hexanediol, 2,2,4-trimethyl-1,3-pentanediol, 1,2-cyclohexanediol, 1,4-cyclohexanediol, 1,4-bis(hydroxymethyl)cyclohexane, neopentyl glycol hydroxypivalate, 2,2-bis(4-hydroxyphenyl) propane, 2,2-bis[4-(2-hydroxypropyl)phenyl]propane, diethylene glycol, triethylene glycol, tetraethylene glycol, dipropylene glycol, tripropylene glycol, tetrapropylene glycol, 3-thiopentane-1,5-diol, and polyethylene glycols, polypropylene glycols and polytetrahydrofurans having molecular weights of from 200 to 10,000. Besides the homopolymers of ethylene oxide or propylene oxide, it is also possible to use block copolymers of ethylene oxide or propylene oxide or copolymers containing incorporated ethylene oxide or propylene oxide groups. Examples of parent alcohols having more than two OH groups are trimethylolpropane, glycerol, pentaerythritol, 1,2,5-pentanetriol, 1,2,6-hexanetriol, triethoxycyanuric acid, sorbitan, sugars, such as sucrose, glucose and mannose. It is of course also possible to use the polyhydric alcohols in the form of corresponding ethoxylates or propoxylates after reaction with ethylene oxide or propylene oxide. The polyhydric alcohols can also first be converted into the corresponding glycidyl ethers by reaction with epichlorohydrin.

Other suitable crosslinking agents are the vinyl esters or the esters of monohydric, unsaturated alcohols with ethylenically unsaturated $C_3$–$C_6$-carboxylic acids, for example acrylic acid, methacrylic acid, itaconic acid, maleic acid or fumaric acid. Examples of such alcohols are allyl alcohol, 1-buten-3-ol, 5-hexen-1-ol, 1-octen-3-ol, 9-decen-1-ol, dicyclopentenyl alcohol, 10-undecen-1-ol, cinnamyl alcohol, citronellol, crotyl alcohol or cis-9-octadecen-1-ol. However, it is also possible to esterify the monohydric, unsaturated alcohols using polybasic carboxylic acids, for example malonic acid, tartaric acid, trimellitic acid, phthalic acid, terephthalic acid, citric acid or succinic acid.

The crosslinking agents used can also be esters of unsaturated carboxylic acids with the polyhydric alcohols described above, for example oleic acid, crotonic acid, cinnamic acid or 10-undecenoic acid.

Also suitable are straight-chain or branched, linear or cyclic, aliphatic or aromatic hydrocarbons having at least two double bonds, which, in the case of aliphatic hydrocarbons, must not be conjugated, for example divinylbenzene, divinyltoluene, 1,7-octadiene, 1,9-decadiene, 4-vinyl-1-cyclohexene, trivinylcyclohexane or polybutadienes having molecular weights of from 200 to 20,000.

Other suitable crosslinking agents are acrylamides, methacrylamides and N-allylamines of at least difunctional amines. Examples of such amines are 1,2-diaminomethane, 1,2-diaminoethane, 1,3-diaminopropane, 1,4-diaminobutane, 1,6-diaminohexane, 1,12-dodecanediamine, piperazine, diethylenetriamine or isophoronediamine. Also suitable are the amides made from allylamine and unsaturated carboxylic acids, such as acrylic acid, methacrylic acid, itaconic acid, maleic acid or at least dibasic carboxylic acid as described above.

Furthermore, triallylamine and triallylmonoalkylammonium salts, for example triallylmethylammonium chloride or methylsulfate, are suitable as crosslinking agents.

Also suitable are N-vinyl compounds of urea derivatives, at least difunctional amides, cyanurates or urethanes, for example of urea, ethyleneurea, propyleneurea or tartaramide, for example N,N'-divinylethyleneurea or N,N'-divinylpropyleneurea.

Also suitable are alkylenebisacrylamides, such as methylenebisacrylamide and 1,1'-bis (2,2'- and 1,1'-bis(3,3'-vinylbenzimidazol-2-one)-1,4-butane Examples of other suitable crosslinking agents are alkylene glycol di(meth)acrylates, such as ethylene glycol diacrylate, ethylene glycol dimethacrylate, tetraethylene glycol diacrylate, tetraethylene glycol dimethacrylate, diethylene glycol diacrylate, diethylene glycol dimethacrylate, vinyl acrylate, allyl acrylate, allyl methacrylate, divinyl dioxane, pentaerythritol triallyl ether and mixtures of these crosslinking agents.

Other suitable crosslinking agents are tetraallylsilane and tetravinylsilane.

Examples of particularly preferred crosslinking agents are methylenebisacrylamide, triallylamine and triallylalkylammonium salts, divinylimidazole, N,N'-divinylethyleneurea, products of the reaction of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin. Very particularly preferred crosslinking agents are methylenebisacrylamide, N,N'-divinylethyleneurea and acrylic esters of glycol, butanediol, trimethylolpropane or glycerol or acrylic esters of glycol, butanediol, trimethylolpropane or glycerol of the reaction with ethylene oxide and/or epichlorohydrin.

The crosslinking agent is especially soluble in the reaction medium. If the solubility of the crosslinking agent in the reaction medium is low, it can be dissolved in a monomer or monomer mixture or alternatively metered in dissolved in a solvent which is miscible with the reaction medium. Particular preference is given to crosslinking agents which are soluble in the monomer mixture.

The content of crosslinking agent may affect the solution viscosity of the novel polymers to a great extent.

The further, free-radical-polymerizable monomers (c) may be the following: N-vinylacetamide, N-methyl-N-vinylacetamide, acrylamide, methacrylamide, N,N-dimethylacrylamide, N-methylolmethacrylamide, N-vinylformamide, N-vinyloxazolidone and N-vinyltriazole. The group of monomers (c) includes, for example, acrylonitrile, methacrylonitrile, acrylic and methacrylic esters derived from monohydric $C_1$- to $C_{18}$-alcohols, hydroxy-$C_2$- to $C_4$-alkylesters of acrylic acid and methacrylic acid, maleic anhydride, vinyl esters, 2-acrylamido-2-methylpropanesulfonic acid and/or vinylphosphoric acid. Also suitable are esters of acrylic acid and methacrylic acid with fatty alcohol ethoxylates and fatty alcohol propoxylates in which the fatty alcohol component has 10 to 20 carbon atoms and the ethylene oxide or propylene oxide content is from 1 to 20 mol %. Such alcohol components are obtained, for example, by reacting $C_{10}$- to $C_{20}$-fatty alcohols with ethylene oxide and/or propylene oxide and esterifying the resultant alkoxylated fatty alcohols using acrylic acid or methacrylic acid. The use of these comonomers gives crosslinked copolymers which have high electrolyte resistance. The monomers from group (c) are used in an amount of from 0 to 30% by weight, preferably up to 15% by weight. If they are used for the modification of the copolymers from (a) and (b), the lower limit is 5% by weight, based on the monomer mixture. The total of the percentages for monomers (a), (b) and (c) is in all cases 100%. Examples of esters of acrylic acid and methacrylic acid are methyl acrylate, ethyl acrylate, methyl methacrylate, 2-ethylhexyl acrylate, stearyl acrylate, stearyl methacrylate and the acrylic esters of the isomeric butyl alcohols. Suitable hydroxy-$C_2$- to $C_4$-alkyl esters of acrylic acid and methacrylic acid are, for example, hydroxyethyl acrylate, hydroxypropyl acrylate, hydroxybutyl acrylate, hydroxyethyl methacrylate, hydroxypropyl methacrylate and hydroxybutyl methacrylate. Of the vinyl esters, preference is given to vinyl acetate and vinyl propionate. Other suitable monomers are olefins, such as ethylene or propylene, styrene and alkylethylene glycol acrylates and ethacrylates having 1 to 50 ethylene glycol units.

Suitable initiators for the free-radical polymerization are ater-soluble and water-insoluble peroxo and/or azo compounds, or example alkali metal or ammonium peroxydisulfates, hydrogen peroxide, dibenzoyl peroxide, tert-butyl perpivalate, 2,2'-azobis(2,4-dimethylvaleronitrile), tert-butyl peroxyneodecanoates, tert-butyl per-2-ethylhexanoate, di-tert-butyl peroxide, tert-butyl hydroperoxide, azobisisobutyronitrile, azobis(2-amidinopropane) dihydrochloride and 2,2'-azobis(2-methylbutyronitrile). Also suitable are initiator mixtures or redox initiator systems, for example ascorbic acid/iron(II) sulfate/sodium peroxodisulfate, tert-butyl hydroperoxide/sodium disulfite, and tert-butyl hydroperoxide/sodium hydroxymethanesulfonate. The initiators can be used in the conventional amounts, for example from 0.05 to 7% by weight, based on the amount of the monomers to be polymerized.

The concomitant use of redox coinitiators, for example benzoin, dimethylaniline and complexes and salts of heavy metals, such as copper, cobalt, manganese, nickel and chromium and in particular iron, which are soluble in organic solvents allows the half-value periods of said peroxides, in particular the hydroperoxides, to be reduced, so that, for example, tert-butyl hydroperoxide is effective even at 100° C. in the presence of 5 ppm of copper(II) acetylacetonate.

Preference is given to sparingly water-soluble or water-insoluble initiators.

The polymerization can, if desired, also be carried out in the presence of polymerization regulators in order to regulate the molecular weight of the polymers. If it is desired to prepare particularly low-molecular-weight copolymers, larger amounts of polymerization regulators are used, while the preparation of high-molecular-weight copolymers is carried out in the presence of only small amounts of polymerization regulators or in the absence of these substances. Examples of polymerization regulators are 2-mercaptoethanol, mercaptopropanols, mercaptobutanols, thioglycolic acid, n-dodecyl mercaptan, tert-dodecyl mercaptan, thiophenol, mercaptopropionic acid, allyl alcohol and acetaldehyde. The polymerization regulators are used in an amount of from 0 to 10% by weight, preferably from 0 to 5% by weight, based on the monomers employed.

The polymers obtainable by the novel process are suitable for use as viscosity modifiers (emulsifiers and dispersion auxiliaries), as W/O and O/W emulsifiers and generally as process assistants, finishing assistants or as superabsorbents, furthermore as detergent additives, such as encrustation and dye transfer inhibitors, as retention aids in papermaking, as flocculants in water treatment or for use in the area of food technology, for example as filtration aids or complexing agents.

The polymers are also particularly suitable as thickeners and gelling agents in cosmetic formulations, especially for skin and hair cosmetic preparations, such as hair treatments, hair lotions, hair rinses, hair emulsions, tip fluids, leveling agents for permanent waves, hot-oil treatments, setting lotions or hair sprays, in particular in skin and hair conditioners.

Depending on the area of application, the hair cosmetic preparations can be applied as sprays, foams, gels, gel sprays or mousses.

The polymers are furthermore suitable as auxiliaries in pharmaceutical formulations, for example as tablet disintegrants.

The polymers prepared in accordance with the invention are white, free-flowing powders having a uniform morphology and virtually no tendency to stick.

EXAMPLES

General Procedure

Carbon dioxide was introduced into an autoclave and brought into the supercritical state and to the reaction temperature by increasing the pressure and temperature. The starting materials were then metered in in the form of a mixture in a single feed. The reaction mixture was stirred at 600 rpm. The residence time in the reactor was 10 hours. The mixture was then cooled to room temperature and decompressed, giving a loose, white powder with no tendency toward aggregation and having particle sizes in the range from 10 to 500 μm.

The respective composition and reaction conditions are shown in the table below. The amount data for the peroxo free-radical initiators in each case relate to 75% strength by weight solutions in aliphatic compounds.

TABLE

| Example | Composition | Pressure during the reaction [bar] | Reaction temperature [° C.] |
|---|---|---|---|
| 1 | 1.5 g N-methyl-N-vinylimidazolium methosulfate[1]<br>13.5 g N-vinylpyrrolidone<br>0.06 g triallylamine<br>0.15 g tert-butyl peroxypivalate<br>0.03 g 2,2'-azobis (2-amidinopropane) dihydrochloride<br>155 g carbon dioxide | 160 | 60 |
| 2 | 3 g N-methyl-N-vinylimidazolium methosulfate[2]<br>13.5 g N-vinylpyrrolidone<br>0.86 g N-vinylcaprolactam<br>0.085 g divinylethyleneurea<br>0.145 g tert-butyl peroxypivalate | 160 | 60 |

[1] dissolved in 1.4 g of water
[2] dissolved in 2.8 g of water

We claim:

1. A process for the preparation of pulverulent, cationic, crosslinked polymers based on monoethylenically unsaturated monomers containing a quaternized or quaternizable nitrogen atom, which comprises carrying out the polymerization in supercritical carbon dioxide as inert diluent with mixing at from 31° C. to 150° C. and above 73 bar.

2. A process as claimed in claim 1 for the preparation of polymers comprising
   - (a1) from 5 to 99.99% by weight of a free-radical-polymerizable monomer containing a quaternized or quaternizable nitrogen atom, or a mixture of such monomers,
   - (a2) from 5 to 95% by weight of an N-vinyllactam,
   - (b) from 0.01 to 20% by weight of a monomer having at least two ethylenically unsaturated groups which effects crosslinking, and
   - (c) from 0 to 50% by weight of a further free-radical-polymerizable monomer.

3. A process as claimed in claim 1, in which the quaternizable nitrogen atoms are quaternized by reaction with methyl chloride, dimethyl sulfate or diethyl sulfate.

* * * * *